United States Patent
Ko et al.

(10) Patent No.: US 9,289,458 B2
(45) Date of Patent: Mar. 22, 2016

(54) METHOD FOR PRODUCING BLACK GINSENG HAVING INCREASED GINSENOSIDE RH2 COMPONENT CONTENT, AND BLACK GINSENG PRODUCT PRODUCED BY MEANS OF THE PRODUCTION METHOD

(75) Inventors: Sang Wha Ko, Incheon (KR); Wan Seok Ko, Seoul (KR)

(73) Assignees: Sang Wha Ko, Incheon (KR); Wan Seok Ko, Seoul (KR); Yan Yu An, Jilin Province (CN)

( * ) Notice: Subject to any disclaimer, the term of this patent is extended or adjusted under 35 U.S.C. 154(b) by 0 days.

(21) Appl. No.: 14/232,482

(22) PCT Filed: Jul. 13, 2012

(86) PCT No.: PCT/KR2012/005598
§ 371 (c)(1),
(2), (4) Date: Jan. 13, 2014

(87) PCT Pub. No.: WO2013/009137
PCT Pub. Date: Jan. 17, 2013

(65) Prior Publication Data
US 2014/0127331 A1   May 8, 2014

(30) Foreign Application Priority Data
Jul. 14, 2011   (KR) .................. 10-2011-0070038

(51) Int. Cl.
*A61K 36/258* (2006.01)
*A23L 1/30* (2006.01)
*A23L 1/212* (2006.01)

(52) U.S. Cl.
CPC ............. *A61K 36/258* (2013.01); *A23L 1/2121* (2013.01); *A23L 1/2123* (2013.01); *A23L 1/3002* (2013.01)

(58) Field of Classification Search
None
See application file for complete search history.

(56) References Cited

U.S. PATENT DOCUMENTS

2009/0104323 A1 *  4/2009  Lee ................................. 426/392

FOREIGN PATENT DOCUMENTS

| KR | 10-0543862 B1 | 1/2006 |
| KR | 10-0600795 B1 | 7/2006 |
| KR | 10-0729214 B1 | 6/2007 |
| KR | 10-2007-0077819 A | 7/2007 |
| KR | 10-2009-0109986 A | 10/2009 |
| KR | 10-2010-0098208 A | 9/2010 |
| WO | WO 2008100052 A1 * | 8/2008 |

* cited by examiner

*Primary Examiner* — Amy L Clark
(74) *Attorney, Agent, or Firm* — STIP Law Group, LLC

(57) ABSTRACT

The method for producing black ginseng having increased ginsenoside Rh2 component content of the present invention comprises the steps of: (a) washing ginseng and drying same under predetermined time conditions in a shaded place; and (b) repeatedly carrying out a plurality of times a process in which the dried ginseng is steamed under predetermined temperature and time conditions and is dried under conditions that differ from the temperature and time conditions during the steaming. By producing black ginseng via a plurality of steps under fixed conditions in this way, it is possible to increase the content of ginsenoside Rh2 as compared with hitherto.

3 Claims, 1 Drawing Sheet

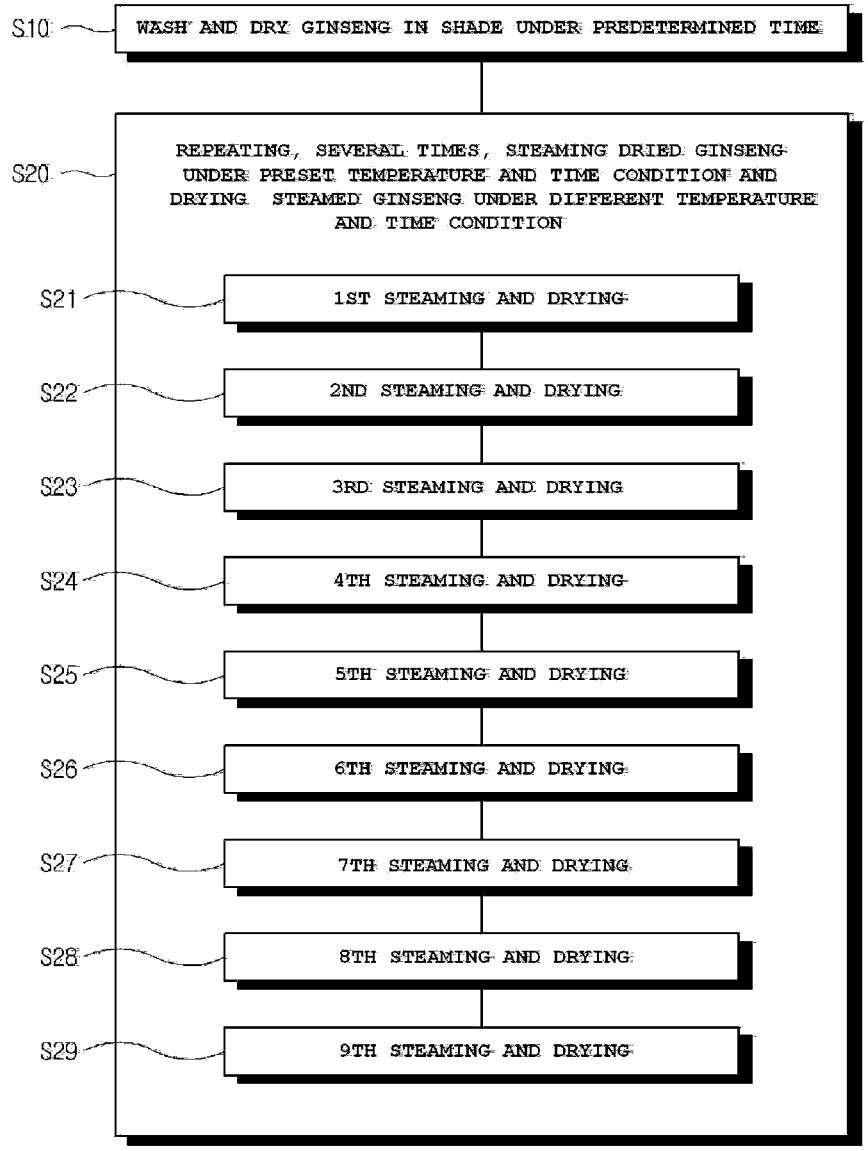

METHOD FOR PRODUCING BLACK GINSENG HAVING INCREASED GINSENOSIDE RH2 COMPONENT CONTENT, AND BLACK GINSENG PRODUCT PRODUCED BY MEANS OF THE PRODUCTION METHOD

CROSS-REFERENCE TO RELATED APPLICATION

This application claims the benefit of Korean Patent Application No. 10-2011-0070038, filed on Jul. 14, 2011 in the Korean Intellectual Property Office, the disclosure of which is incorporated herein by reference.

TECHNICAL FIELD

The present invention relates to a method of producing black ginseng having an increased ginsenoside Rh2 content and a black ginseng product produced by the same method.

BACKGROUND ART

Ginseng is an Oriental medical herb, the efficacy and availability of which have been known for a long time, and is typically distributed in the form of fresh ginseng, white ginseng or steamed red ginseng.

Steamed red ginseng is produced by steaming and drying ginseng several times, and black ginseng is produced by steaming and drying ginseng more times than steamed red ginseng.

Through the steaming and drying processes, saponin, crude saponin and ginsenoside Rh2 which have not been present in ginseng are produced. A large amount of saponin, crude saponin and ginsenoside Rh2 is contained in black ginseng which underwent more steaming and drying processes than steamed red ginseng.

Black ginseng refers to ginseng which is made black through the multiple steaming and drying processes. Since ginsenoside, a readily available active component of ginseng, did not leak through the several steaming and drying processes, the content of the active component is increased compared to that of either fresh ginseng or steamed red ginseng.

Recently, interest in such black ginseng is rapidly increasing since ginsenoside content thereof is significantly greater than that of steamed red ginseng that has been widely consumed as processed ginseng foods.

Korean Patent No. 10-0496418 (MANUFACTURING METHOD OF BLACK ROOTLETS OF GINSENG) discloses a method of producing black ginseng black ginseng fine roots includes: repeating, four times, the following processes of washing fine roots of ginseng with distilled water one to three times, first steaming the washed fine roots of the ginseng at 60 to 70° C. for 1.5 to 2 hours, and drying the fine roots of ginseng to a moisture content of 28%; repeating, four times, the following processes of steaming the fine roots of ginseng in a high-pressure steamer at a temperature of 135° C. for 2 to 3 hours and drying the steamed fine roots of ginseng in a hot-wind rotational dryer at 60 to 70° C. so as to have a moisture content of 25%; drying the resultant fine roots of ginseng in a bulk dryer so as to have a final moisture content of 14%; and removing impurities.

In addition, Korean Patent Application Publication No. 2003-0005089 (METHOD FOR MENUFACTURING RED GINSENG) disclosed a method of producing black ginseng or black ginseng fine roots. This method includes washing fresh ginseng and repeating, seven times or more, the following processes of separating fine roots from main roots and drying the fine roots and main roots to a moisture content of 14% or less. Consequently, the fresh ginseng is converted into steamed red ginseng and then the steamed red ginseng is turned black while the major components inside saponin stay through these processes.

However, in the black ginseng or the black ginseng fine roots produced by the technology disclosed in the above-mentioned document, as for the contents of several kinds of ginsenoside in ginseng, only the contents of certain components were increased slightly from or similar to those of fresh ginseng or steamed red ginseng of the related art.

Nevertheless, it is real that the contents of active components were increases than those of fresh ginseng or steamed red ginseng of the related art. Therefore, black ginseng is gaining more popularity.

Therefore, at the point of time when the efficacies of black ginseng are being proven gradually, there is a need for research on novel black ginseng, the efficacies of which are significantly better than those of conventional black ginseng.

DISCLOSURE

Technical Problem

The present invention has been made to solve the foregoing problems with the related art, and therefore an aspect of the present invention is to provide a method of producing black ginseng having an increased ginsenoside Rh2 content and a black ginseng product produced by the same method, in which the ginsenoside Rh2 content can be increased to be greater than that of the related art since black ginseng is produced through multiple steps under predetermined conditions.

Technical Solution

In an aspect of the present invention, provided is a method of producing black ginseng in which ginsenoside Rh2 content is increased. The method includes: (a) step of washing ginseng and drying the washed ginseng in a shade under a predetermined time condition; and (b) step of repeating, several times, steaming the dried ginseng under a predetermined temperature and time condition and drying the steamed ginseng under a predetermined temperature and time condition that differs from the predetermined temperature and time condition of the steaming. The (b) step includes: (b1) first steaming the ginseng that is dried at the (a) step at 98 to 102° C. for 10 to 12 hours and drying the steamed ginseng at to 56° C. for 48 to 72 hours; (b2) second steaming the ginseng that is dried at the (b1) step at 96 to 100° C. for 8 to 10 hours and drying the steamed ginseng at 54 to 56° C. for 20 to 24 hours; (b3) third steaming the ginseng that is dried at the (b2) step at 94 to 96° C. for 8 to 10 hours and drying the steamed ginseng at 54 to 56° C. for 20 to 24 hours; (b4) fourth steaming the ginseng that is dried at the (b3) step at 90 to 92° C. for 8 to 10 hours and drying the steamed ginseng at 54 to 56° C. for 10 to 12 hours; (b5) fifth steaming the ginseng that is dried at the (b4) step at 88 to 90° C. for 8 to 10 hours and drying the steamed ginseng at 54 to 56° C. for 8 to 10 hours; (b6) sixth steaming the ginseng that is dried at the (b5) step at 85 to 87° C. for 8 to 10 hours and drying the steamed ginseng at 54 to 56° C. for 8 to 10 hours; (b7) seventh steaming the ginseng that is dried at the (b6) step at 85 to 87° C. for 8 to 10 hours and drying the steamed ginseng at 54 to 56° C. for 8 to 10 hours; (b8) eighth steaming the ginseng that is dried at the (b7) step at 78 to 80° C. for 8 to 10 hours and drying the steamed ginseng at 54 to 56° C. for 7 to 8 hours; and (b9) ninth steaming the ginseng that is dried at the (b8) step at 78 to 80° C. for 7 to 8 hours and drying the steamed ginseng at 54 to 56° C. for 10 to 12 hours.

The predetermined time condition at the (a) step may range from 24 to 48 hours.

The (b) step may be carried out in a digital temperature controlled steamer from which steam does not leak to the outside.

Advantageous Effects

According to the present invention, it is possible to increase the content of ginsenoside Rh2 that suppresses either the multiplication of cancer cells or the growth of tumors to be greater than that of the related art by producing black ginseng through the multiplicity of processes under preset conditions.

DESCRIPTION OF DRAWINGS

FIG. 1 is a flowchart of a method of producing black ginseng having an increased ginsenoside Rh2 content according to an embodiment of the present invention.

DESCRIPTION OF THE REFERENCE NUMERALS IN THE DRAWINGS

S10: Step of washing ginseng and drying the washed ginseng in a shade for a predetermined time S20: Step of repeating, several times, steaming the dried ginseng at a predetermined temperature and drying the steamed ginseng under a set condition, the temperature and time of which differ from those of the steaming step

BEST MODE

Reference will now be made to exemplary embodiments of the present invention in conjunction with the accompanying drawings.

FIG. 1 is a flowchart of a method of producing black ginseng having an increased ginsenoside Rh2 content according to an embodiment of the present invention.

Referring to this figure, the method of producing black ginseng according to this embodiment is devised to produce a black ginseng product having an increased ginsenoside Rh2 content, for example, a black ginseng extraction, and includes step S10 of washing ginseng and drying the washed ginseng in a shade under a predetermined time condition and step S20 of repeating, several times, steaming the dried ginseng at a predetermined temperature and drying the steamed ginseng under a condition, the temperature and time of which are different from the steaming step.

At the step S10 of washing ginseng and drying the washed ginseng in a shade under a predetermined time condition, the predetermined time may range from 24 to 48 hours.

That is, it is possible to dry the ginseng in the shade for a preset time ranging from one to two days. The time may be determined based on the moisture content of the ginseng. A drying time of about two days will be required for ginseng that has a higher moisture content, whereas the drying time of about one day will be required for ginseng that has a lower moisture content.

The step S20 of repeating, several times, steaming the dried ginseng at a predetermined temperature and drying the steamed ginseng under a set condition, the temperature and time of which differ from those of the steaming step can include first steaming and drying step S21 to ninth steaming and drying step S29. In other words, the nine steaming and drying processes can be carried out under different temperature and time conditions.

The step S20 can be carried out in a digital temperature controlled steamer from which steam does not leak to the outside, or in a typical steamer.

When the method of producing black ginseng according to this embodiment is carried out in the digital temperature controlled steamer from which steam does not leak to the outside, it is convenient to set a time and a temperature and accurately carry out the process. Accordingly, an improvement in the quality of a black ginseng product can be expected.

The step S20 will be described in more detail.

The step S21 includes first steaming of the dried ginseng at 98 to 102° C. (preferably at a temperature of 100° C.) for 10 to 12 hours (preferably for 10 hours), and after the first steaming, drying the steamed ginseng at 54 to 56° C. (preferably at a temperature of 55° C.) for 48 to 72 hours (preferably for 72 hours).

The step S22 includes second steaming of the dried ginseng that has undergone the step S21 at 96 to 100° C. (preferably at a temperature of 98° C.) for 8 to 10 hours (preferably for 10 hours), and after the second steaming, drying the steamed ginseng at 54 to 56° C. (preferably at a temperature of 55° C.) for 20 to 24 hours (preferably for 24 hours).

The step S23 includes third steaming of the dried ginseng that has undergone the step S22 at 94 to 96° C. (preferably at a temperature of 95° C.) for 8 to 10 hours (preferably for 10 hours), and after the third steaming, drying the steamed ginseng at 54 to 56° C. (preferably at a temperature of 55° C.) for 20 to 24 hours (preferably for 24 hours).

The step S24 includes fourth steaming of the dried ginseng that has undergone the step S23 at 90 to 92° C. (preferably at a temperature of 91° C.) for 8 to 10 hours (preferably for 10 hours), and after the fourth steaming, drying the steamed ginseng at 54 to 56° C. for 10 to 12 hours (preferably for 12 hours).

The step S25 includes fifth steaming of the dried ginseng that has undergone the step S24 at 88 to 90° C. (preferably at a temperature of 89° C.) for 8 to 10 hours (preferably for 10 hours), and after the fifth steaming, drying the steamed ginseng at 54 to 56° C. for 8 to 10 hours (preferably for 10 hours).

The step S26 includes sixth steaming of the dried ginseng that has undergone the step S25 at 85 to 87° C. (preferably at a temperature of 86° C.) for 8 to 10 hours (preferably for 10 hours), and after the sixth steaming, drying the steamed ginseng at 54 to 56° C. for 8 to 10 hours (preferably for 10 hours).

The step S27 includes seventh steaming of the dried ginseng that has undergone the step S26 at 85 to 87° C. (preferably at a temperature of 86° C.) for 8 to 10 hours (preferably for 10 hours), and after the seventh steaming, drying the steamed ginseng at 54 to 56° C. for 8 to 10 hours (preferably for 10 hours).

The step S28 includes eighth steaming of the dried ginseng that has undergone the step S27 at 78 to 80° C. (preferably at a temperature of 79° C.) for 8 to 10 hours (preferably for 10 hours), and after the eighth steaming, drying the steamed ginseng at 54 to 56° C. for 7 to 8 hours (preferably for 8 hours).

The step S29 includes ninth steaming of the dried ginseng that has undergone the step S28 at 78 to 80° C. (preferably at a temperature of 79° C.) for 7 to 8 hours (preferably for 8 hours), and after the ninth steaming, drying the steamed ginseng at 54 to 56° C. (preferably at a temperature of 55° C.) for 10 to 12 hours (preferably for 12 hours).

These data can be arranged as presented in Table 1 below.

TABLE 1

| Step | Steaming temperature (preferable temperature) | Steaming time (preferable time) | Drying temperature (preferable temperature) | Drying time (preferable time) |
|---|---|---|---|---|
| a  | —              | —         | shade       | 24 to 48 hrs |
| b1 | 98 to 102° C. (100° C.) | 10 to 12 hrs (10 hrs) | 54 to 56° C. (55° C.) | 48 to 72 hrs (72 hrs) |
| b2 | 96 to 100° C. (98° C.) | 8 to 10 hrs (10 hrs) | 54 to 56° C. (55° C.) | 20 to 24 hrs (24 hrs) |
| b3 | 94 to 96° C. (95° C.) | 8 to 10 hrs (10 hrs) | 54 to 56° C. (55° C.) | 20 to 24 hrs (24 hrs) |
| b4 | 90 to 92° C. (91° C.) | 8 to 10 hrs (10 hrs) | 54 to 56° C. | 10 to 12 hrs (12 hrs) |
| b5 | 88 to 90° C. (89° C.) | 8 to 10 hrs (10 hrs) | 54 to 56° C. | 8 to 10 hrs (10 hrs) |
| b6 | 85 to 87° C. (86° C.) | 8 to 10 hrs (10 hrs) | 54 to 56° C. | 8 to 10 hrs (10 hrs) |
| b7 | 85 to 87° C. (86° C.) | 8 to 10 hrs (10 hrs) | 54 to 56° C. | 8 to 10 hrs (10 hrs) |
| b8 | 78 to 80° C. (79° C.) | 8 to 10 hrs (10 hrs) | 54 to 56° C. | 7 to 8 hrs (8 hrs) |
| b9 | 78 to 80° C. (79° C.) | 7 to 8 hrs (8 hrs) | 54 to 56° C. | 10 to 12 hrs (12 hrs) |

Before describing specific embodiments of the present invention, components contained in the black ginseng according to the present invention will be described in brief as follows.

Among the components of the black ginseng according to the present invention, ginsenoside Rh2 shows the greatest change in the content. It is known that the efficacy of ginsenoside Rh2 is to suppress either the multiplication of cancer cells or the growth of tumors.

In addition, effects of ginsenoside Rb1 include inhibition of the central nervous system, tranquilization, inhibition of the feeding center, promotion of neurotransmitter secretion, promotion of cholesterol metabolism, promotion of biosynthesis of nucleic acid, proteins and lipids, improvement in brain function, inhibition of aggressive actions, protection of the liver, and promotion of anti-oxidation.

Furthermore, it is known that the effects of ginsenoside Rb2 include inhibition of the central nervous system, promotion of protein biosynthesis, anti-diabetic efficacy, promotion of sugar and lipid metabolism, lowering of cholesterol levels, anti-arteriosclerosis, inhibition of tumor angiogenesis, balancing of nitrogen metabolism.

In addition, ginsenoside Rc provides several effects, such as inhibition of the central nervous system, promotion of protein biosynthesis, and enhancement of sperm motility. It is known that the effects of ginsenoside Rd include a defense against radiation damage, protection of nerve cells, immunomodulation and anti-oxidation.

Furthermore, ginsenoside Re provide several effects, such as anti-diabetic efficacy, reduction of insulin resistance, protection of nerve cells, enhancement of the ability of sperm to fertilize and anti-oxidation. Ginsenoside Rf provides the effect of anti-nociception.

In addition, ginsenoside Rg1 provides several effects, such as excitement of the central nervous system, improvements in memory and learning functions, protection of brain cells, promotion of the multiplication of nerve cells, stress relaxation, inhibition of stress-based eating disorders, immunomodulation, stress relaxation, inhibition of aggregation of platelets and vasodilation. Ginsenoside Rg2 has several effects, such as reduction of memory decay due to vascular brain damage, protection of nerve cells and promotion of multiplication of endothelial cells. It is known that the effects of ginsenoside Rg3 include inhibition of the transfer of cancer cells, vascular relaxation, protection against brain cell damage, suppression of the resistance to anticancer drugs and inhibition of aggregation of platelets.

Reference will now be made to specific examples according to the present invention.

EXAMPLE 1

First, a material was prepared by purchasing a preset amount of 5-year ginseng at a market, clearly washing the ginseng, and then drying the washed ginseng in the shade for about 30 hours.

Afterwards, nine different steaming and drying processes were carried out. Specifically, at the first steaming and drying processes, the dried ginseng was steamed at 100° C. for 10 hours, followed by drying at 55° C. for 50 hours. At the second steaming and drying processes, the first-steamed ginseng was steamed again at 98° C. for 9 hours, followed by drying at 55° C. for 21 hours. At the third steaming and drying processes, the second-steamed ginseng was steamed at 95° C. for 9 hours, followed by drying at 55° C. for 22 hours. At the fourth steaming and drying processes, the third-steamed ginseng was steamed at 91° C. for 9 hours, followed by drying at 55° C. for 11 hours. At the fifth steaming and drying processes, the fourth-steamed ginseng was steamed at 89° C. for 9 hours, followed by drying at 55° C. for 9 hours. At the sixth steaming and drying processes, the fifth-steamed ginseng was steamed at 86° C. for 9 hours, followed by drying at 55° C. for 9 hours. At the seventh steaming and drying processes, the sixth-steamed ginseng was then steamed at 86° C. for 9 hours, followed by drying at 55° C. for 9 hours. At the eighth steaming and drying processes, the seventh-steamed ginseng was steamed at 79° C. for 9 hours, followed by drying at 55° C. for 7 hours. At the ninth steaming and drying processes, the eighth-steamed ginseng was steamed at 79° C. for 7 hours, followed by drying at 55° C. for 11 hours.

The composition of black ginseng powder produced in Example 1 above was analyzed at the Cultivated Ginseng-Mountain Cultivated Ginseng Research Center of Chung-Ang University, and the results are presented in Table 2 below.

TABLE 2

| Analysis items | Unit | Result | Analysis method |
|---|---|---|---|
| Compound K | mg/g | N.D | HPLC analysis |
| Ginsenoside-$Rh_2$ |  | 5.561 |  |
| —$Rh_1$ |  | 0.607 |  |
| —$Rg_2$ |  | 1.042 |  |
| —$Rg_3$ |  | 2.726 |  |
| —$Rg_1$ |  | 1.618 |  |
| —Rf |  | 1.145 |  |
| —Re |  | 1.066 |  |
| —Rd |  | 0.049 |  |
| —Rc + $Rb_2$ |  | 6.532 |  |
| —$Rb_3$ |  | N.D |  |
| —$Rb_1$ |  | 0.498 |  |

It was possible to produce a black ginseng product having an increased ginsenoside Rh2 content by applying the above-mentioned method.

EXAMPLE 2

First, a material was prepared by purchasing a preset amount of 4 year ginseng at the market, clearly washing the purchased ginseng, and then drying the washed ginseng in the shade for about 40 hours.

Afterwards, nine different steaming and drying processes were carried out. Specifically, at the first steaming and drying processes, the dried ginseng was steamed at 100° C. for 10 hours, followed by drying at 55° C. for 72 hours. At the second steaming and drying processes, the first-steamed ginseng was steamed at 98° C. for 10 hours, followed by drying at 55° C. for 24 hours. At the third steaming and drying processes, the second-steamed ginseng was steamed at 95° C. for 10 hours, followed by drying at 55° C. for 24 hours. At the fourth steaming and drying processes, the third-steamed ginseng was steamed at 91° C. for 10 hours, followed by drying at 55° C. for 12 hours. At the fifth steaming and drying processes, the fourth-steamed ginseng was fifthly steamed at 89° C. for 10 hours, followed by drying at 55° C. for 10 hours. At the sixth steaming and drying processes, the fifth-steamed ginseng was sixthly steamed at 86° C. for 10 hours, followed by drying at 55° C. for 10 hours. At the seventh steaming and drying processes, the sixth-steamed ginseng was steamed at 86° C. for 10 hours, followed by drying at 55° C. for 10 hours. At the eighth steaming and drying processes, the seventh-steamed ginseng was eighthly steamed at 79° C. for 10 hours, followed by drying at 55° C. for 8 hours. At the ninth steaming and drying processes, the eighth-steamed ginseng was steamed at 79° C. for 8 hours, followed by drying at 55° C. for 12 hours.

The composition of black ginseng powder produced in Example 2 above was analyzed at the Cultivated Ginseng-Mountain Cultivated Ginseng Research Center of Chung-Ang University, and the results are presented in Table 3 below.

| Analysis items | Unit | Result | Analysis method |
| --- | --- | --- | --- |
| Compound K | mg/g | N.D | HPLC analysis |
| Ginsenoside-$Rh_2$ | | 4.522 | |
| —$Rh_1$ | | 1.203 | |
| —$Rg_2$ | | 1.183 | |
| —$Rg_3$ | | 5.908 | |
| —$Rg_1$ | | 1.069 | |
| —Rf | | 1.101 | |
| —Re | | 0.972 | |
| —Rd | | 0.048 | |
| —Rc + $Rb_2$ | | 0.933 | |
| —$Rb_3$ | | 0.395 | |
| —$Rb_1$ | | 0.405 | |

It was possible to produce a black ginseng product having an increased ginsenoside Rh2 content by applying the above-mentioned method.

For reference, Korean Patent No. 10-0840003 which was filed by the applicant also disclosed a related-art method of producing black ginseng by repeating steaming and drying processes several times. However, the black ginseng produced in that fashion contained only a small amount of active component, i.e. ginsenoside Rh2 was from 0.8 to 1.3 mg/g.

However, a black ginseng product produced by the method of producing black ginseng according to the present invention has a ginsenoside Rh2 content ranging from 4.5 to 5.5 mg/g. It can be appreciated that the ginsenoside Rh2 content significantly increased compared to that of a black ginseng product of the related art.

As set forth above, this embodiment can increase the content of ginsenoside Rh2 that suppresses either the multiplication of cancer cells or the growth of tumors compared to the related art by producing black ginseng through the multiplicity of processes under preset conditions.

The present invention is not limited to the foregoing certain embodiment. Obviously many modifications and alterations are possible to a person skilled in the art without departing from the scope of the present invention defined in the appended claims, and such modifications and alterations shall fall within the scope of the claims.

The invention claimed is:

1. A method of producing black ginseng, comprising:
   (a) the step of washing ginseng and drying the washed ginseng in shade for a predetermined time to provide dried ginseng; and
   (b) the step of repeating, several times, steaming the dried ginseng of (a) step at a predetermined temperature and time and drying the steamed ginseng at a predetermined temperature and time that is different from the predetermined temperature and time of the steaming,
   wherein the (b) step comprises:
   (b1) first, steaming the ginseng that is dried in the (a) step at 98 to 102° C. for 10 to 12 hours and drying the first steamed ginseng at 54 to 56° C. for 48 to 72 hours;
   (b2) second, steaming the ginseng that is dried in the (b1) step at 96 to 100° C. for 8 to 10 hours and drying the second steamed ginseng at 54 to 56° C. for 20 to 24 hours;
   (b3) third, steaming the ginseng that is dried in the (b2) step at 94 to 96° C. for 8 to 10 hours and drying the third steamed ginseng at 54 to 56° C. for 20 to 24 hours;
   (b4) fourth, steaming the ginseng that is dried in the (b3) step at 90 to 92° C. for 8 to 10 hours and drying the fourth steamed ginseng at 54 to 56° C. for 10 to 12 hours;
   (b5) fifth, steaming the ginseng that is dried in the (b4) step at 88 to 90° C. for 8 to 10 hours and drying the fifth steamed ginseng at 54 to 56° C. for 8 to 10 hours;
   (b6) sixth, steaming the ginseng that is dried in the (b5) step at 85 to 87° C. for 8 to 10 hours and drying the sixth steamed ginseng at 54 to 56° C. for 8 to 10 hours;
   (b7) seventh, steaming the ginseng that is dried in the (b6) step at 85 to 87° C. for 8 to 10 hours and drying the seventh steamed ginseng at 54 to 56° C. for 8 to 10 hours;
   (b8) eighth, steaming the ginseng that is dried in the (b7) step at 78 to 80° C. for 8 to 10 hours and drying the eighth steamed ginseng at 54 to 56° C. for 7 to 8 hours; and
   (b9) ninth, steaming the ginseng that is dried in the (b8) step at 78 to 80° C. for 7 to 8 hours and drying the ninth steamed ginseng at 54 to 56° C. for 10 to 12 hours, wherein ginsenoside Rh2 content is increased to a range from 4.5 mg/g to 5.5 mg/g of said black ginseng.

2. The method according to claim 1, wherein the predetermined time in the (a) step ranges from 24 to 48 hours.

3. The method according to claim 1, wherein the (b) step is carried out in a digital temperature controlled steamer wherein steam within the steamer does not leak outside of the steamer.

* * * * *